US00RE46814E

(19) United States
(12) Reissued Patent
Smith et al.

(10) Patent Number: US RE46,814 E
(45) Date of Reissued Patent: May 1, 2018

(54) MEDICATION DELIVERY DEVICE

(71) Applicants: Christopher James Smith, Holmes Chapel (GB); Michael Heald, Crewe (GB); Stephen David Butler, Staffordshire (GB); Mark Philip Horlock, Cheshire (GB)

(72) Inventors: Christopher James Smith, Holmes Chapel (GB); Michael Heald, Crewe (GB); Stephen David Butler, Staffordshire (GB); Mark Philip Horlock, Cheshire (GB)

(73) Assignee: SANOFI-AVENTIS DEUTSCHLAND GMBH, Frankfurt am Main (DE)

(21) Appl. No.: 14/677,006

(22) Filed: Apr. 2, 2015

Related U.S. Patent Documents

Reissue of:
(64) Patent No.: 8,834,430
Issued: Sep. 16, 2014
Appl. No.: 13/943,036
Filed: Jul. 16, 2013

(51) Int. Cl.
*A61M 5/315* (2006.01)

(52) U.S. Cl.
CPC ..... *A61M 5/31585* (2013.01)

(58) Field of Classification Search
CPC ..... A61M 5/31543
(Continued)

(56) References Cited

U.S. PATENT DOCUMENTS 533,575 A 2/1895 Wilkens
5,226,895 A 7/1993 Harris
(Continued)

FOREIGN PATENT DOCUMENTS

EP 0937471 8/1999
EP 0937476 8/1999
(Continued)

OTHER PUBLICATIONS

Form PCT/IB326, Notification Concerning Transmittal of International Preliminary Report on Patentability for Int. App. No. PCT/EP2011/059565, mailed Dec. 27, 2012.
(Continued)

*Primary Examiner* — Cary Wehner
(74) *Attorney, Agent, or Firm* — McDonnell Boehnen Hulbert & Berghoff LLP

(57) ABSTRACT

A medication delivery device is provided which is switchable between an operational state and a resetting state and which comprises a housing having a proximal end and a distal end, a piston rod being moveable in a distal direction with respect to the housing for medication delivery, a conversion element adapted to at least partially convert a rotational movement of the piston rod into an axial movement of the piston rod, coupling means prevented from rotational movement with respect to the housing and adapted to engage with the conversion element in the operational state, a drive assembly comprising at least two drive assembly members and adapted for moving the piston rod in the distal direction, and a resilient member adapted to provide a force on the drive assembly for engagement of the drive assembly members. In the operational state of the device the coupling means is engaged with the conversion element, the conversion element thereby being prevented from rotation with respect to the housing. In the resetting state of the device the coupling means is disengaged from the conversion element under force of the resilient member, the conversion element thereby being allowed to rotate with respect to the housing and thereby allowing a resetting of the device.

18 Claims, 8 Drawing Sheets

(58) Field of Classification Search
USPC ..... 604/218
See application file for complete search history.

(56) References Cited

U.S. PATENT DOCUMENTS

| | | | | |
|---|---|---|---|---|
| 5,279,586 | A | 1/1994 | Balkwill | |
| 5,304,152 | A | 4/1994 | Sams | |
| 5,320,609 | A | 6/1994 | Haber et al. | |
| 5,383,865 | A | 1/1995 | Michel | |
| 5,480,387 | A | 1/1996 | Gabriel et al. | |
| 5,505,704 | A | 4/1996 | Pawelka et al. | |
| 5,582,598 | A | 12/1996 | Chanoch | |
| 5,626,566 | A | 5/1997 | Petersen et al. | |
| 5,674,204 | A | 10/1997 | Chanoch | |
| 5,688,251 | A | 11/1997 | Chanoch | |
| 5,827,232 | A * | 10/1998 | Chanoch et al. | 604/208 |
| 5,921,966 | A | 7/1999 | Bendek et al. | |
| 5,961,495 | A | 10/1999 | Walters et al. | |
| 6,004,297 | A | 12/1999 | Steenfeldt-Jensen et al. | |
| 6,193,698 | B1 | 2/2001 | Kirchhofer et al. | |
| 6,221,046 | B1 | 4/2001 | Burroughs et al. | |
| 6,235,004 | B1 | 5/2001 | Steenfeldt-Jensen et al. | |
| 6,248,095 | B1 | 6/2001 | Giambattista et al. | |
| 6,899,698 | B2 | 5/2005 | Sams | |
| 6,936,032 | B1 | 8/2005 | Bush, Jr. et al. | |
| 7,241,278 | B2 | 7/2007 | Moller | |
| 7,850,662 | B2 | 12/2010 | Veasey et al. | |
| 8,187,233 | B2 | 5/2012 | Harms et al. | |
| 8,366,680 | B2 * | 2/2013 | Raab | A61M 5/31555 604/207 |
| 2002/0052578 | A1 | 5/2002 | Moller | |
| 2002/0120235 | A1 | 8/2002 | Enggaard | |
| 2003/0050609 | A1 | 3/2003 | Sams | |
| 2004/0059299 | A1 | 3/2004 | Moller | |
| 2004/0210199 | A1 | 10/2004 | Atterbury et al. | |
| 2004/0267207 | A1 | 12/2004 | Veasey et al. | |
| 2005/0113765 | A1 | 5/2005 | Veasey et al. | |
| 2006/0153693 | A1 * | 7/2006 | Fiechter et al. | 417/63 |
| 2006/0206057 | A1 * | 9/2006 | DeRuntz | A61M 5/31551 604/224 |
| 2007/0016143 | A1 | 1/2007 | Miller et al. | |
| 2009/0275914 | A1 * | 11/2009 | Harms et al. | 604/506 |
| 2009/0275916 | A1 | 11/2009 | Harms et al. | |
| 2010/0106099 | A1 * | 4/2010 | Christiansen et al. | 604/208 |

FOREIGN PATENT DOCUMENTS

| | | | |
|---|---|---|---|
| EP | 1923085 | A1 | 5/2008 |
| WO | 93/07922 | A1 | 4/1993 |
| WO | 99/38554 | | 8/1999 |
| WO | 99/38554 | A1 | 8/1999 |
| WO | 01/10484 | | 2/2001 |
| WO | 02/30495 | A2 | 4/2002 |
| WO | 2006/084876 | A1 | 8/2006 |
| WO | 2008/074897 | A1 | 6/2008 |

OTHER PUBLICATIONS

International Search Report for Int. App. No. PCT/EP2011/059565, completed Aug. 31, 2011.

* cited by examiner

MEDICATION DELIVERY DEVICE

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CROSS REFERENCE TO RELATED APPLICATIONS

The present application is a continuation of U.S. patent application Ser. No. 13/701,987, filed Dec. 4, 2012, entitled "Medication Delivery Device," which is a U.S. National Phase Application pursuant to 35 U.S.C. § 371 of International Application No. PCT/EP2011/059565 filed Jun. 9, 2011, which claims priority to European Patent Application No. 10165637.9 filed on Jun. 11, 2010. The entire disclosure contents of these applications are herewith incorporated by reference into the present application.

FIELD OF INVENTION

The present invention relates to a medication delivery device for delivering a dose of a medication, for example to a reusable pen-type injection device. The device may be configured to dispense variable doses of the medication where a user can vary the size of a dose. Alternatively, the device may be a fixed dose device, in particular a device configured to dispense doses of the drug which may not be varied by the user. The drug delivery device may be a manually, in particular a non-electrically driven device.

BACKGROUND

In particular, the present invention may relate to such medication delivery devices where a user may set a dose of medication to be delivered from a multi-dose cartridge. Most preferably, the medication delivery device comprises a single- or multi-dose medication cartridge which can be replaced when the medication for example has been fully dispensed or has passed its date of expiry.

Medication delivery devices of the kind mentioned above have become widespread where regular injections by persons without formal medical training occur. This is increasingly common among those having diabetes where self-treatment enables such persons to conduct effective management of their diabetes.

As a result of environmental and economical reasons, medication delivery devices of the type mentioned above have been developed to allow only a part of the device to be discarded, usually the medication cartridge only, and the other part to be reused. This provides the additional requirement for such a medication delivery device that the resetting of a drive mechanism, when a new cartridge is attached to or inserted into the medication delivery device, needs to be easy and unambiguous, thereby reducing the possibility of damage to the drive assembly.

SUMMARY

It is an object of the present invention to disclose a medication delivery device comprising a reset mechanism which facilitates a resetting of the medication delivery device and which nevertheless is cost-effective.

This object is achieved with the medication delivery device according to claim 1. Further aspects and variations of the invention derive from the depending claims.

The medication delivery device is switchable between an operational state and a resetting state and comprises:

a housing having a proximal end and a distal end, a piston rod being moveable in a distal direction with respect to the housing for medication delivery, a conversion element adapted to at least partially convert a rotational movement of the piston rod into an axial movement of the piston rod, a coupling means prevented from rotational movement with respect to the housing and adapted to engage with the conversion element in the operational state, a drive assembly comprising at least two drive assembly members and adapted for moving the piston rod in the distal direction, a resilient member adapted to provide a force on the drive assembly for engagement of the drive assembly members, wherein in the operational state of the device the coupling means is engaged with the conversion element, the conversion element thereby being prevented from rotation with respect to the housing, and in the resetting state of the device the coupling means is disengaged from the conversion element on the force of the resilient member, the conversion element thereby being allowed to rotate with respect to the housing and thereby allowing a resetting of the device.

Such a medication delivery device may have the advantage that the resilient member fulfils double functionalities.

In a first aspect, the resilient member provides a force on the drive assembly for engagement of the drive assembly members. This may enable the drive assembly members to interact with each other for moving the piston rod in the distal direction during medication delivery. In a second aspect the resilient member may provide a force such that the coupling means becomes disengaged from the conversion element during switching of the device from the operational state into the resetting state. In the resetting state, the conversion element may be allowed to freely rotate with respect to the housing. According to this concept, the medication delivery device is resettable in the resetting state by moving the piston rod in the proximal direction into the housing and thereby rotating the conversion element. This may provide for a smooth and easy reset action and may aid all users, but particularly those with impaired dexterity. Furthermore the device may be cost-effective with the resilient member fulfilling double duties because no additional component is needed.

The term "housing" shall preferably mean any exterior housing ("main housing", "body", "shell") or interior housing ("insert", "inner body"). The housing may be designed to enable the safe, correct, and comfortable handling of the medication delivery device or any of its mechanism.

The term "conversion element" shall preferably mean any component designed to guide the piston rod in the operational state during medication delivery, thereby converting rotational movement of the piston rod into axial movement of the piston rod, preferably in distal direction with respect to the housing. For this purpose the conversion element preferably comprises a shape for interacting with a corresponding shape of the piston rod. For example, the conversion element may be a kind of nut element and the piston rod may be a kind of lead screw. Furthermore, when the conversion element and therefore the medication delivery device are in the operational state, the conversion element may be designed to prevent the resetting of the medication delivery device, i.e. it directly or indirectly prevents a movement of the piston rod in the proximal direction. Additionally, when the conversion element and therefore the medication delivery device are in the resetting state, the conversion element may be designed to enable the resetting of the medication delivery device, i.e. it directly or indirectly allows a movement of the piston rod in the proximal direction. Hence, the medication delivery device is switchable between the operational state and the resetting state, the conversion element assuming the respective state.

The term "drive assembly" shall preferably mean any assembly in which a first drive assembly member is configured to transfer force, preferably torque, to a second drive assembly member. The transferred force may cause the second drive assembly member to be axially displaced with respect to the housing for dose delivery. Preferably, the drive assembly may drive a piston rod for delivery of a medication.

The term "operational state" according to the present invention shall preferably mean a state of the device, where a dispensing of medication is enabled. Moreover, it preferably means a position of the conversion element in which the conversion element prevents the resetting of the medication delivery device. Preferably, the operational state is furthermore a position or state of the conversion element in which the conversion element guides and/or holds the piston rod. When the medication delivery device is used for dose-setting and/or medication delivery, the conversion element and therefore the medication delivery device are preferably in the operational state.

The term "resetting state" according to the present invention shall preferably mean a state of the device, where a resetting of the drive mechanism is enabled. Moreover, it preferably means a position of the conversion element in which the conversion element allows the resetting of the medication delivery device. The conversion element is preferably in the resetting state when the medication delivery device is disassembled, i.e. the medication receptacle is disengaged from the housing for replacing an old or empty cartridge with a new cartridge filled with medication.

The term "resilient member" according to the present invention shall preferably mean any element that is provided for exerting a force on a component and/or components to ensure that these components are forced together, e.g. into engagement, or forced apart, e.g. out of engagement. For example, the drive assembly members are forced together by the resilient member in the operational state of the device. Besides, the coupling means and the conversion element may be forced apart by the resilient member in the resetting state of the device. Preferably the resilient member may be manufactured from any suitable flexible energy storage material known by a person skilled in the art, e.g. metal, rubber or plastics, and may take any suitable form, e.g. a spring.

The term "coupling means" according to the present invention shall preferably mean any component that is part of the housing, fixed to the housing, engaged with the housing or engaged with a component fixed to the housing such that the coupling means is prevented from rotational movement with respect to the housing.

The term "distal end" according to the present invention shall mean the end of the device or a component of the device which is closest to the dispensing end of the device. Preferably a needle assembly is provided at the distal end of the medication delivery device, the needle of which can be inserted into the skin of a patient for medication delivery.

The term "proximal end" according to the present invention shall mean the end of the device or a component of the device which is furthest away from the dispensing end of the device. Preferably a button or other dosing element is provided at the proximal end of the medication delivery device which may be pushed for dose delivery.

The term "piston rod" according to the present invention shall mean a component adapted to operate through/within the housing and designed to be moveable in axial direction (preferably towards the distal end) through/within the medication delivery device and to translate its axial movement preferably to a piston or bung of the cartridge for the purpose of discharging/dispensing a medication from the cartridge. Said piston rod may be flexible or not. It may be a simple rod, a lead-screw, a part of a rack and pinion system, a part of a worm gear system or the like. The piston rod shall further mean a component having a circular or a non-circular cross-section. It may be made of any suitable material known by a person skilled in the art.

The term "medication", as used herein, preferably means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody, a hormone or an oligonucleotide, or a mixture of the above-mentioned pharmaceutically active compound.

In a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis.

In a further embodiment the pharmaceutically active compound comprises at least one peptide for the treatment and/or prophylaxis of diabetes mellitus or complications associated with diabetes mellitus such as diabetic retinopathy.

In a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(w-carboxyheptadecanoyl) human insulin.

Exendin-4 for example means Exendin-4(1-39), a peptide of the sequence H-His-Gly-Glu-Gly-Thr-Phe-Thr-Ser-Asp- Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-$(Lys)_4$-des Pro36, des Pro37 Exendin-4(1-39)-NH2,
H-$(Lys)_5$-des Pro36, des Pro37 Exendin-4(1-39)-NH2,
des Pro36 [Asp28] Exendin-4(1-39),
des Pro36 [IsoAsp28] Exendin-4(1-39),
des Pro36 [Met(O)14, Asp28] Exendin-4(1 -39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
H-$(Lys)_6$-des Pro36 [Asp28] Exendin-4(1-39)-Lys6-NH2,
des Asp28 Pro36, Pro37, Pro38Exendin-4(1-39)-NH2,
H-$(Lys)_6$-des Pro36, Pro38 [Asp28] Exendin-4(1-39)-NH2,
H-Asn-(Glu)5des Pro36, Pro37, Pro38 [Asp28] Exendin-4 (1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4 (1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4 (1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-$(Glu)_5$-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2) 25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, $Trp(O2)_{25}$, Asp28] Exendin-4(S1-39)-(Lys)6-NH2,
H-Asn-(Glu)5-des Pro36, Pro37, Pro38 [Met(O)14, Trp(O2) 25, Asp28] Exendin-4(1-39)-(Lys)6-NH2;
or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

Turning now again to the design of the medication delivery device, according to a first embodiment the conversion element is permanently prevented from axial movement with respect to the housing, whereby during switching of the device between the operational state and the resetting state the coupling means is axially moved with respect to the housing between a first axial position according to the operational state of the device and a second axial position according to the resetting state of the device. Hence, the coupling means can assume two different axial positions with respect to the housing according to the respective state of the device.

Preferably the medication delivery device in this first embodiment comprises retaining means prevented from axial movement relative to the housing, the conversion element being restrained by the retaining means from moving axially. However, the conversion element is allowed to revolve with respect to the housing. The retaining means can be integrally formed as part of the housing or as a separate member which is secured against axial movement relative to the housing. The retaining means may be designed to surround and border the conversion element such that the conversion element is indirectly secured against axial movement relative to the housing. Nevertheless, the retaining means preferably do not prevent the conversion element from revolving with respect to the housing.

Preferably, according to this first embodiment, in the operational state of the device the coupling means is held in the first axial position. Moreover, during switching of the device between the operational state and the resetting state, the coupling means is axially moved, preferably in distal direction, and brought into the second axial position under force of the resilient member. During switching of the device from the operational state into the resetting state, the force of the resilient member urges the coupling means to disengage from the conversion element. The conversion element and the whole device may be brought into the resetting state, the conversion element being allowed to revolve with respect to the housing.

According to another, second embodiment of the present invention, the coupling means is permanently prevented from axial movement with respect to the housing, and during switching of the device between the operational state and the resetting state the conversion element is axially moved with respect to the housing between a first axial position according to an operational state of the device and a second axial position according to the resetting state of the device. Contrary to the first embodiment explained above, in this second embodiment the conversion element is axially moved during switching of the device between the respective states while the coupling means is the element which is permanently prevented from axial movement relative to the housing. The coupling means can be integrally formed as part of the housing or as separate member which is secured against axial movement with respect to the housing.

According to this second embodiment, in the operational state of the device the conversion element is preferably held in the first axial position. Moreover, during switching of the device between the operational state and the resetting state, the conversion element is axially moved, preferably in distal direction, and brought into the second axial position under force of the resilient member. During switching of the device from the operational state into the resetting state, the force of the resilient member urges the conversion element to be disengaged from the coupling means. The conversion element and the whole device may be brought into the resetting state, the conversion element being free to revolve and rotate relative to the housing.

Preferably the medication delivery device comprises a medication receptacle adapted to be secured to the housing. The term "medication receptacle" in this context shall preferably mean a cartridge containing a medication or a cartridge assembly, most preferably a cartridge holder for receiving a cartridge containing a medication. Preferably, in the operational state of the device, the medication receptacle is secured to the housing thereby holding the coupling means in engagement with the conversion element. In the resetting state of the device the medication receptacle may be removed from the housing thereby allowing disengagement of the coupling means from the conversion element. Preferably, the device is in the operational state when the medication receptacle is secured to the housing and in the resetting state when the medication receptacle is removed from the housing. Switching of the whole device between the two states is achieved by securing or removing the medication receptacle to or from the housing. In particular, on securing a medication receptacle to the device, the device may be switched from the resetting state to the operational state and by removing the medication receptacle from the device, the device may be switched from the operational state to the resetting state.

Furthermore, when the medication receptacle is secured to the housing, the resilient member preferably becomes strained, thereby providing a force on the drive assembly for engagement of the drive assembly members. When the medication receptacle is disengaged from the housing, the resilient member preferably becomes unstrained, the drive assembly members of the drive assembly being allowed and enabled to be disengaged from each other.

The medication receptacle preferably is a cartridge holder which is provided for receiving a cartridge filled with medication. The cartridge holder may be designed to be engaged with a distal end of the housing of the device. Alternatively, the medication receptacle can be a cartridge having first engagement means for engaging second engagement means of the housing of the device. A cartridge filled with medication is preferably a tubular sleeve containing the medication and may be closed by a piston or bung at one end and by a pierceable septum at the other end. When the piston or bung is moved distally in the cartridge, the medication is dispensed, e.g. through a needle which pierces the septum and which is in communication with the medication.

Preferably the conversion element comprises first locking means and the coupling means comprises second locking means, the first and second locking means being adapted to interlock with each other. Preferably, the first and second locking means are formed by at least one of teeth, splines, protrusions, and castellations. In the operational state, the first and second locking means may interlock with each other when the coupling means and the conversion element are engaged. In the resetting state, the first and second locking means may be disengaged when the coupling means and the conversion element are disengaged. By interlocking of the first and second locking means in the operational state a rotational movement of the first and second locking means relative to each other is inhibited. Preferably the first and second locking means are formed such that one locking means engages in a respective negative shape of the other locking means such that the teeth, splines, protrusions and castellations of one locking means locks the other locking means in order to prevent rotational movement with respect to the housing.

Preferably the piston rod is threadedly engaged with the conversion element. The conversion element thereby preferably comprises an inner thread for engaging an outer thread of the piston rod. Optionally, the conversion element comprises a circular or non-circular opening for holding the piston rod with a corresponding circular or non-circular form or a piston rod with a section having the corresponding circular or non-circular form. Accordingly, the conversion element may act, as described above, as "nut means" or a "body nut" for guiding the piston rod and for converting a rotational movement of the piston rod into an axial movement of the piston rod, preferably in distal direction with respect to the housing during the operational state. In the resetting state as mentioned above, the conversion element is free to rotate with respect to the housing, the piston rod being allowed to be moved in the proximal direction into the housing. Thereby, the conversion element, the piston rod and in particular the threaded engagement of the conversion element and the piston rod may be designed such that a proximal movement of the piston rod results in rotational movement of the free-to-rotate conversion element. The thread pitch of the thread of the piston rod preferably is adapted such that the threaded engagement of the conversion element and the piston rod does not inhibit the conversion of proximal movement of the piston rod into rotational movement of the conversion element. Thus, the threaded engagement of the conversion element and the piston rod acts as a non-self-locking engagement at least in the resetting state of the device.

Preferably the medication delivery device comprises a drive member which is a first drive assembly member of the drive assembly and which is adapted to be rotated with respect to the housing, wherein rotational movement of the drive member with respect to the housing is converted into movement of the piston rod in the distal direction with respect to the housing. Preferably, the drive member is at least in the operational state engaged with the piston rod such that rotational movement of the drive member results in a rotational movement of the piston rod, whereby the conversion element, being engaged with the piston rod, urges the piston rod into a helical movement such that a rotational movement of the piston rod is at least partially converted into movement of the piston rod in the distal direction with respect to the housing.

However, in the resetting state the piston rod can be axially moved in proximal direction into the housing, the conversion element thereby freely rotating.

If during proximal movement the piston rod does not rotate with respect to the housing, movement of the piston rod may be not converted into rotational movement of the drive member such that the drive member does not rotate. But if during proximal movement the piston rod does rotate with respect to the housing, movement of the piston rod may be converted into rotational movement of the drive member as the drive member is held in engagement with the piston rod. Thus, in the case that the piston rod rotates during resetting, the drive member may have to be separated and disengaged from other drive assembly members, for example via a separation mechanism of the drive assembly, in order that the drive member can follow rotational movement of the piston rod without being inhibited in rotational movement by other drive assembly members.

Preferably the medication delivery device comprises a rotation member which is a second drive assembly member of the drive assembly and which is adapted to be rotated in a first direction with respect to the housing during setting of a dose of a medication and to be rotated in a second direction with respect to the housing during delivery of the dose, the second direction being opposite to the first direction. Preferably in the operational state the drive member is adapted to follow rotational movement of the rotation member in the second direction with respect to the housing during delivery of the dose. It is preferred, that the drive member and the rotation member are engaged or held in abutment by the force provided by the resilient member during setting and delivery of the dose in the operational state. Preferably, during setting of a dose in the operational state, the rotation member is rotated in the first direction, whereby rotational movement of the drive member can be avoided.

During delivery of the dose in the operational state a rotational movement of the rotation member in the second direction may be transmitted into rotational movement of the drive member in the second direction. That may cause the piston rod to start the helical movement of the kind mentioned above, whereby the piston rod traverses the housing of the device in distal direction and pushes a piston or bung of the cartridge in distal direction thereby expelling a predetermined amount, i.e. a dose, of the medication out of a needle at the distal end of the device.

Preferably the drive member and the rotation member are coupled to one another by a first uni-directional friction clutch mechanism which is configured to permit rotational movement between the drive member and the rotation member during rotation of the rotation member in the first direction for setting of the dose and to prevent relative rotational movement of drive member and rotation member during rotational movement of the rotation member in the second direction for delivery of the dose.

Preferably the drive assembly is designed such that the drive member is engaged with a stop member which is as a third drive assembly member of the drive assembly and which is adapted to prevent rotational movement of the drive member in the first direction with respect to the housing and to permit rotational movement of the drive member in the second direction with respect to the housing. That means, during setting of the dose of medication and rotating the rotation member in the first direction, the drive member is prevented from rotational movement which results in preventing a helical movement of the piston rod in proximal direction and thus prevents inaccuracy of a preset dose. However, during delivery of the dose rotational movement of the rotation member is transmitted into rotational movement of the drive member such that the piston rod is moved in distal direction for expelling a medication out of the device.

Preferably the drive member and the stop member are coupled to one another by a second uni-directional friction clutch mechanism, which is configured to prevent relative rotational movement between the drive member and the stop member in the first direction with respect to the housing and to permit relative rotational movement between the drive member and the stop member in the second direction with respect to the housing.

Further features, refinements and expediencies become apparent from the following description of the exemplary embodiments in connection with the figures.

DETAILED DESCRIPTION

Figure 1:
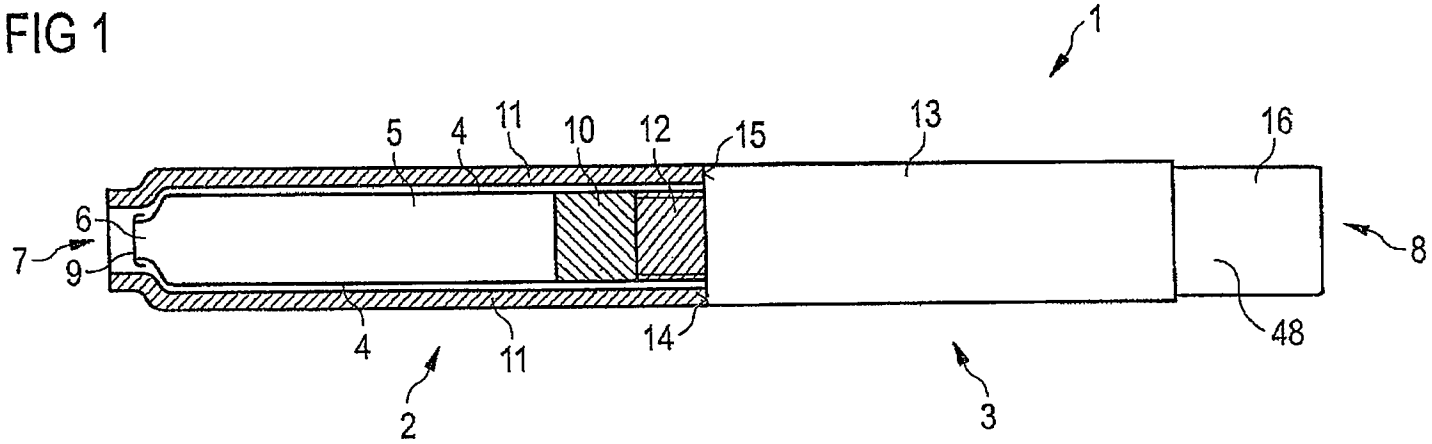
FIG. 1 schematically shows a partly sectional side view of an exemplary embodiment of a medication delivery device.

Turning now to FIG. 1, a medication delivery device 1 comprises a medication receptacle 2 and a drive assembly 3. The medication receptacle 2 comprises a cartridge 4. Medication 5 is retained in the cartridge 4. The medication 5 is preferably liquid medication. The cartridge 4 preferably comprises a plurality of doses of the medication 5. The medication 5 may comprise for example insulin, heparin, growth hormones or any other composition of the type named above. The cartridge 4 has an outlet 6 at its distal end. Medication 5 can be dispensed from the cartridge through outlet 6. The device 1 may be a pen-type device, in particular a pen-type injector. The device 1 may be a disposable or a reusable device. The device 1 may be a device configured to dispense fixed doses of the medication or variable, preferably user-settable, doses. The device 1 may be a needle-based or a needle free device. The device 1 may be an injection device.

In FIG. 1, the distal end of the device 1 was assigned reference numeral 7 and the proximal end of the device was assigned reference numeral 8.

The outlet 6 may be covered by a membrane 9, which protects medication 5 against external influences during storage of the cartridge. For medication delivery, membrane 9 may be opened, e.g. pierced. For example, membrane 9 may be pierced by a needle unit (not explicitly shown). The needle unit may be (releasably) attached to the distal end of the medication receptacle 2. The needle unit may provide for fluid communication from the inside of the cartridge 4 to the outside of the cartridge through outlet 6.

A piston 10 is retained within the cartridge 4. The piston 10 is movable with respect to the cartridge. The piston 10 may seal the medication 5 within the cartridge. The piston 10 expediently seals the interior of the cartridge 4 proximally. Movement of the piston 10 with respect to the cartridge 4 in the distal direction causes medication 5 to be dispensed from the cartridge through outlet 6 during operation of the device.

The medication receptacle 2 furthermore comprises a cartridge retaining member 11. The cartridge 4 is retained within the cartridge retaining member 11. The cartridge retaining member 11 may stabilize the cartridge 4 mechanically. Additionally or alternatively, the cartridge retaining member 11 may be provided with a fixing member (not explicitly shown) for attaching the medication receptacle 2 to the drive assembly 3.

The medication receptacle 2 and the drive assembly 3 are secured to one another, preferably releasably secured. A medication receptacle 2 which is releasably secured to the drive assembly may be detached from the drive assembly 3, for example in order to allow for providing for a new cartridge 4, if all of the doses of medication which once were in the cartridge formerly attached to the drive assembly 3 have already been dispensed. The cartridge retaining member 11 may be releasably secured to the drive assembly 3 via a thread, for example.

Alternatively, the cartridge retaining member 11 may be dispensed with. It is particularly expedient, in this case, to apply a robust cartridge 4 and to attach the cartridge directly to the drive assembly 3.

The drive assembly 3 is configured for transferring force, preferably user-exerted force, particularly preferably manually exerted force, to the piston 10 for displacing the piston 10 with respect to the cartridge 4 in the distal direction. A dose of medication may be dispensed from the cartridge in this way. The size of the delivered dose may be determined by the distance by which the piston 10 is displaced with respect to the cartridge 4 in the distal direction.

Furthermore, the drive assembly comprises a piston rod 12. The piston rod 12 may be configured for transferring force to the piston 10, thereby displacing the piston 10 in the distal direction with respect to the cartridge 4. A distal end face of the piston rod 12 may be arranged to abut a proximal end face of the piston 10. A bearing member (not explicitly shown) may be arranged to advance the piston 10, preferably to abut the proximal end face of the piston 10. The bearing member may be arranged between piston 10 and piston rod 12. The bearing member may be fixed to the piston rod 12 or a separate member. If the piston rod 12 is configured to be rotated during operation of the device, for example during dose delivery, it is particularly expedient to provide for a bearing member. The bearing member may be displaced together with the (rotating) piston rod 12 with respect to the housing. The piston rod 12 may be rotatable with respect to the bearing member. In this way, the risk that the rotating piston rod 12 drills into the piston and thereby damages the piston is reduced. Accordingly, while the piston rod 12 rotates and is displaced with respect to the housing, the bearing member is preferably only displaced, i.e. does not rotate. The piston rod 12 may be bounded by the bearing member.

The drive assembly 3 comprises a housing 13 which the piston rod 12 may be retained in. A proximal end side 14 of the medication receptacle 2 may be secured to the drive assembly 3 at a distal end side 15 of the housing 13, for example via a threaded connection. Housing 13, cartridge 4 and/or cartridge retaining member 11 may have a tubular shape.

The drive assembly 3 comprises a dose part 16. The dose part 16 is movable with respect to the housing 13. The dose part 16 may be movable in the proximal direction with respect to the housing for setting of a dose of the medication 5 which is to be delivered and in the distal direction with respect to the housing for delivery of the set dose. The dose part 16 is preferably connected to the housing 13. The dose part 16 may be secured against rotational movement with respect to the housing. The dose part 16 may be moved (displaced) between a proximal end position and a distal end position with respect to the housing 13 (not explicitly shown). The distance by which the dose part is displaced with respect to the housing during setting of the dose may determine a size of the dose. The proximal end position and the distal end position may be determined by a respective stop feature which may limit the proximal or distal travel of the dose member with respect to the housing. The device 1 may be a variable dose device, i.e. a device configured for delivering doses of medication of different, preferably user-settable, sizes. Alternatively, the device may be a fixed dose device.

The device 1 may be a manually, in particular non-electrically, driven device. The (user-applied) force which causes the dose part 16 to be moved with respect to the housing 13 in the distal direction may be transferred to the piston rod 12 by the drive assembly 3. For this purpose, drive assembly members may be provided which are not explicitly shown in FIG. 1. The drive assembly 3 is preferably configured to not move the piston rod 12 with respect to the housing 13 when the dose part is moved in the proximal direction with respect to the housing for setting of the dose.

Figure 2:
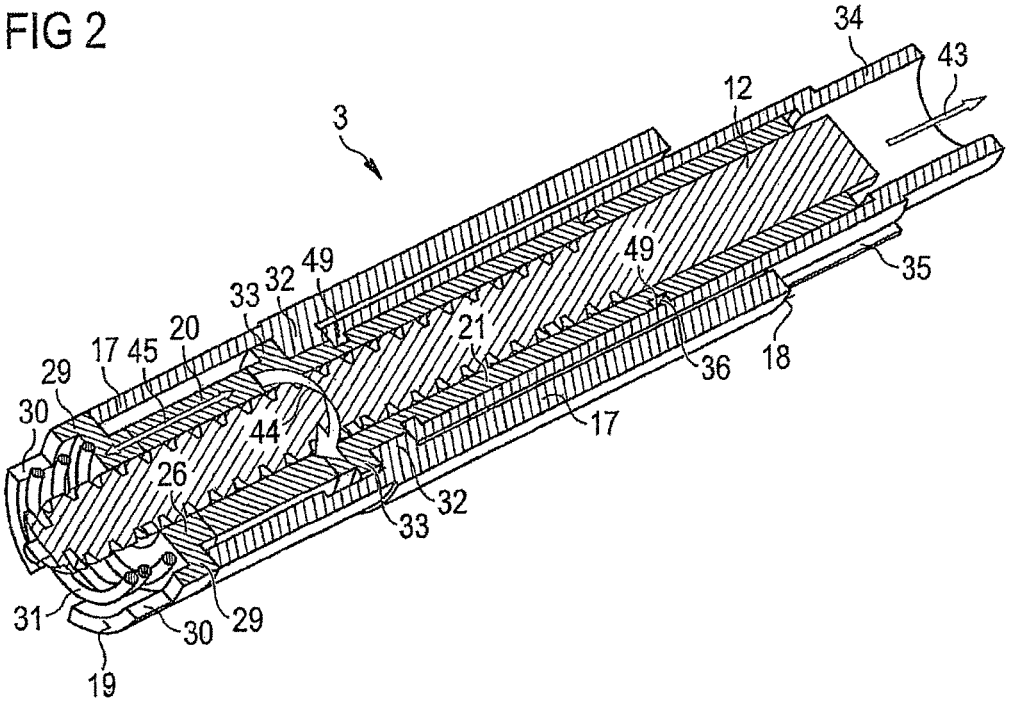
FIG. 2 schematically shows a perspective sectional view of a part of a drive assembly with schematically indicated movements of elements thereof during setting of a dose.
Figure 3:
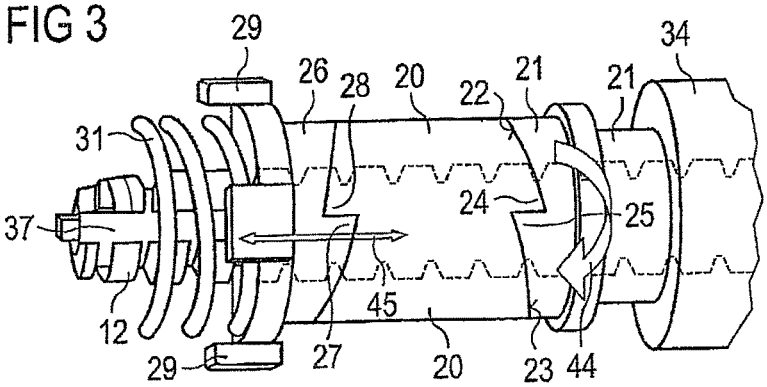
FIG. 3 schematically shows a more detailed side view of a part of FIG. 2.

An embodiment of a drive assembly 3 which is suitable for being implemented in the medication delivery device 1 as described above is described in connection with FIGS. 2 and 3.

The drive assembly 3 comprises a housing part 17. The housing part 17 has a proximal end 18 and a distal end 19. The housing part 17 may be (outer) housing 13 of FIG. 1, a part thereof or an insert within housing 13, the insert being preferably secured against rotational and axial movement with respect to housing 13. The housing part 17 may be an insert sleeve, for example. The insert sleeve may be snap-fitted or glued to housing 13, for example. The housing part 17 may have a tubular shape. Housing part 17 may comprise outer fixing elements (not shown), for example snap-fit elements, for fixing housing part 17 to housing 13.

The piston rod 12 is retained in the housing 13, preferably within housing part 17. The piston rod 12 is driven in the distal direction with respect to the housing part 17 during dose delivery.

The drive assembly furthermore comprises a drive member 20 which is a first drive assembly member of the drive assembly 3. Drive member 20 is retained within the housing part 17. Drive member 20 is configured to transfer force, preferably torque, to the piston rod 12. The transferred force may cause the piston rod 12 to be displaced in the distal direction with respect to the housing part 17 for dose delivery.

Drive member 20 is rotatable with respect to housing part 17. The drive member 20 may engage the piston rod 12. Rotational movement of the drive member 20, for example rotational movement in a second direction may be converted into distal movement of the piston rod 12 with respect to the housing part 17. This is explained in more detail below.

The drive assembly furthermore comprises a rotation member 21 which is a second drive assembly member of the drive assembly 3. The rotation member 21 is rotatable with respect to the housing part 17 in a first direction, in particular for setting of a dose of the medication, and in a second direction, in particular for delivering the set dose. The second direction is opposite to the first direction. According to FIGS. 2 and 3, the first direction may be counter-clockwise and the second direction may be clockwise as seen from the proximal end of the device, for example.

Drive member 20, rotation member 21 and/or piston rod 12 are preferably configured to be rotatable about a (common) rotation axis. The rotation axis may extend through drive member 20, rotation member 21 and/or piston rod 12. The rotation axis may be the main longitudinal axis of the piston rod 12. The rotation axis may run between the proximal end and the distal end of the housing part 17.

The rotation member 21 is coupled to the drive member 20 by a uni-directional clutch mechanism, in particular a friction clutch mechanism. This clutch mechanism permits rotational movement of the rotation member 21 with respect to the drive member 20 when the rotation member 21 rotates in the first direction with respect to the housing part 17. The clutch mechanism prevents rotational movement of the rotation member 21 with respect to the drive member 20, when the rotation member 21 rotates in the second direction with respect to the housing part 17. The drive member 20 may thus follow rotational movement of the rotation member 21 in the second direction with respect to the housing part 17.

The drive member 20 is arranged to abut and/or engage the rotation member 21 and, in particular, engages rotation member 21. The drive member 20 comprises a toothing 22 at one end, e.g. its proximal end. The rotation member 21 comprises a toothing 23 at one end which end faces the drive member 20, e.g. its distal end. Toothing 22 comprises a plurality of teeth 24. Toothing 23 comprises a plurality of teeth 25. Teeth 24 and/or 25 may extend along the rotation axis. Toothings 22 and 23 may be configured to mate with one another.

The teeth 24 may be circumferentially disposed on the drive member 20, particularly at the end of the drive member 20 which faces the rotation member 21. The teeth 25 may be circumferentially disposed on the rotation member 21, particularly at the end of the rotation member 21 which faces the drive member 20.

When the steep end faces of two teeth abut and the rotation member 21 is rotated further on in the second direction, the steep sides stay in abutment and drive member 20 follows the rotation of rotation member 21. When the rotation member 21 rotates in the first direction, the ramp of the teeth—which ramps, in particular, run obliquely with respect to the rotation axis—slide along each other and, inconsequence, the rotation member 21 may rotate with respect to the drive member 20.

The drive assembly 3 furthermore comprises a stop member 26 which is a third drive assembly member of the drive assembly 3. The drive member 20 may be arranged between the stop member 26 and the rotation member 21. The stop member 26 is configured for preventing rotational movement of the drive member 20 in the first direction with respect to the housing part 17 during setting of a dose, i.e. when the rotation member 21 rotates in the first direction. Thus, the rotation member 21 may rotate in the first direction with respect to the housing part 17, whereas the drive member 20 and the stop member 26 do not rotate.

The stop member 26 is coupled to the drive member 20 by another uni-directional clutch mechanism, in particular a friction clutch mechanism. This clutch mechanism prevents rotational movement of the drive member 20 with respect to the stop member 26 when the rotation member 21 rotates in the first direction with respect to the housing part 17. The clutch mechanism permits rotational movement of the drive member 20 with respect to the stop member 26, when the rotation member 21 rotates in the second direction with respect to the housing part 17.

Thus, the rotation member 21 may rotate with respect to the drive member 20 and the stop member 26 in the first direction during setting of the dose, with rotation of the drive member 20 being prevented by its interaction with the stop member 26, and rotation member 21 as well as drive member 20 may rotate with respect to the stop member 26 in the second direction during delivery of the dose.

The stop member 26 may be arranged to abut and/or engage the drive member 20 during setting of the dose and, preferably, during delivery of the dose. The stop member 26 has a toothing 27 at one end which faces the drive member 20, e.g. its proximal end. The teeth may be ramp-shaped with a steep side and a less steep ramp. The teeth may be azimuthally disposed along the stop member 26, in particular on the perimeter of the stop member 26.

Drive member 20 has a toothing 28 at one end which faces the stop member 26, e.g. its distal end. Toothings 22 and 28 of the drive member 20 are oppositely disposed. Toothing 28 may be configured in accordance with toothing 23 of the rotation member 21. Toothing 22 may be configured in accordance with toothing 27 of the stop member 26. Toothings 27 and 28, in particular the steep sides of the teeth, do cooperate, e.g. abut, for preventing rotation of the drive member 20 with respect to the housing part 17 and, in particular, with respect to the stop member 26 in the first direction.

Stop member 26 is preferably secured against rotational movement with respect to the housing part 17. Stop member 26 may be fixed to the housing or integrated into the housing. Stop member 26 may be fixed against displacement with respect to the housing part 17 or displacement with respect to the housing part 17 may be allowed.

As it is illustrated in the present embodiment, stop member 26 is displaceable with respect to the housing but non-rotatable with respect to the housing part 17. For that purpose, one or a plurality of, preferably oppositely disposed, guide features, for example guide lugs 29, are provided in the stop member 26. The respective guide feature 29 engages a corresponding guide slot 30 which may be provided in the housing, e.g. in housing part 17. This can be seen in FIGS. 2 and 3. A guide feature 29 cooperates with a guide slot 30 to prevent rotational movement of the stop member 26 with respect to the housing part 17, with axial movement of the stop member 26 with respect to the housing being allowed. The axial movement of the stop member 26 may compensate for play between components of the drive assembly 3 during operation.

From the group comprising drive member 20, stop member 26 and rotation member 21 one or more members, preferably two members or three members, may be axially displaceable (double arrow 45 in FIGS. 2 and 3) with respect to the housing part 17 and, preferably, with respect to the piston rod 12. Therein, the drive member 20 and another one of the recited members 21 or 26 may be axially displaceable with respect to the housing. The remaining member may be secured against axial displacement or may also be axially displaceable during operation of the drive assembly 3 for medication delivery. Accordingly, if the drive member 20 and the stop member 26 are axially displaceable, the rotation member 21 may be axially secured or axially displaceable and so on. Play between the components caused by relative (axial) movement of components of the clutch mechanism with respect to the housing can be compensated for in this way. The distance by which the respective components may be axially displaced with respect to the housing may correspond to the (maximum) depth of a tooth of the respective toothing 22 or 28 of the drive member 20. Alternatively, the distance may be greater than the (maximum) depth of a tooth of the respective toothing.

Furthermore, the drive assembly 3 comprises a resilient member 31, preferably a spring member. The resilient member 31 may be biased during medication delivery operation of the drive assembly 3. The resilient member 31 may provide for a force that tends to keep drive assembly members in engagement, i.e. the drive member 20 in engagement with the stop member 26 and/or the rotation member 21. The force may be exerted along the rotation axis. In the situation shown in FIGS. 2 and 3, this force may be exerted in the proximal direction. The resilient member 31 may be a helical (coil) spring. The resilient member 31 may be a compression spring.

The resilient member 31 may keep the drive member 20 and the stop member 26 in (permanent) mechanical contact, e.g. in abutment, with each other during setting and delivery of a dose of the medication. Alternatively or additionally, the resilient member 31 may keep the drive member 20 and the rotation member 21 in (permanent) mechanical contact, preferably abutment, with each other during setting and delivery of a dose of the medication.

The resilient member 31 may be integrated within stop member 26 or a separate component. The resilient member 31 may be arranged on the distal end side of the stop member 26.

The drive assembly 3 furthermore comprises a support member 32. Support member 32 is expediently fixed against axial and rotational movement with respect to the housing part 17 or integrated into housing part 17. Support member 32 is arranged on that side of the drive member 20 which is remote from the stop member 26. Support member 32 may be a protrusion, for example a ring-like protrusion. Rotation member 21 may extend through an opening in support member 32. The support member 32 may provide for a counter force to the force which is exerted by the resilient member 31. Permanent abutment of the rotation member 21 with the drive member 20 and of the drive member 20 with the stop member 26 during setting and delivery of medication is facilitated in this way.

The rotation member 21 has an (radially) outwardly protruding member 33, for example a flange portion. The protruding member 33 is expediently provided for abutting support member 32, in particular the distal end side of support member 32.

The drive assembly 3 furthermore comprises a dose member 34. Dose member 34 may be dose part 16 or may be a part of the dose part 16 of FIG. 1. Dose member 34 is movable with respect to the housing in the proximal direction (arrow 43) for setting of a dose and for delivery of the dose. For example, the dose member 34 may be moved in the proximal direction with respect to the housing part 17 during dose setting and in the distal direction with respect to the housing part 17 during dose delivery. The dose member 34 may engage the housing part 17 or, alternatively, another part of housing 13 (not explicitly shown). Dose member 34 is preferably secured against rotational movement with respect to the housing part 17. The dose member 34 may comprise a guide feature 35, for example a guide lug or a guide slot, that engages another guide feature, for example a guide slot or a guide lug, respectively, that is provided in the housing part 17 or the housing 13.

Dose member 34 may be moved in the proximal direction and in the distal direction with respect to rotation member 21. Dose member 34 is arranged to be coupleable and is preferably (permanently) coupled to rotation member 21 such that movement of the dose member, e.g. in the proximal direction with respect to the housing part 17, for setting a dose of the medication is converted into rotational movement of the rotation member 21 in the first direction (arrow 44) and movement of the dose member, e.g. in the distal direction with respect to the housing part 17, for delivering the dose is converted into rotational movement of the rotation member 21 in the second direction opposite to the first direction.

The rotation member 21 may be provided with an (outer) thread 36. Thread 36 may be engaged with one of or a plurality of engagement members 49 of dose member 34. The respective engagement member may be arranged on the inside of the dose member. The respective engagement member may be a thread or a part of a thread, for example. Thus, dose member 34 and rotation member 21 may be threadedly coupled, in particularly threadedly engaged. The rotation member 21 may be arranged inside the dose member 34.

The drive member 20 and the piston rod 12 are configured for rotational movement of the drive member 20 with respect to the housing being converted into rotational movement of the piston rod 12 with respect to the housing. The drive member 20 may engage the piston rod 12. The piston rod 12 is displaceable with respect to the drive member 20 along a displacement axis. Presently, the displacement axis runs along the rotation axis. The drive member 20 may be splined to the piston rod 12, for example.

The piston rod 12 may be threadedly coupled to the housing 13. The piston rod 12 may be provided with an outer thread, for example. The piston rod 12 comprises an engagement track 37, preferably two oppositely disposed engagement tracks 37, on the outside. The (respective) engagement track 37 may interrupt the outer thread of the piston rod 12. The (respective) engagement track 37 preferably extends along the axis along which the piston rod 12 is displaceable with respect to the housing 13 and, in particular, with respect to the drive member 20.

Rotational movement of the drive member 20 with respect to the housing may thus be converted into rotational movement of the piston rod 12 with respect to the housing and the rotational movement of the piston rod 12 is, on account of the threaded engagement of the piston rod 12 and the housing (part), converted into movement of the piston rod 12 with respect to the housing in the distal direction.

The dose part 16 (cf. FIG. 1) may comprise a dose button 48. Dose button 48 may be configured to be gripped by a user. Dose button 48 may be arranged and connected to the dose member 34 at the proximal end. Dose button 48 and dose member 34 may be unitary.

Figure 4:
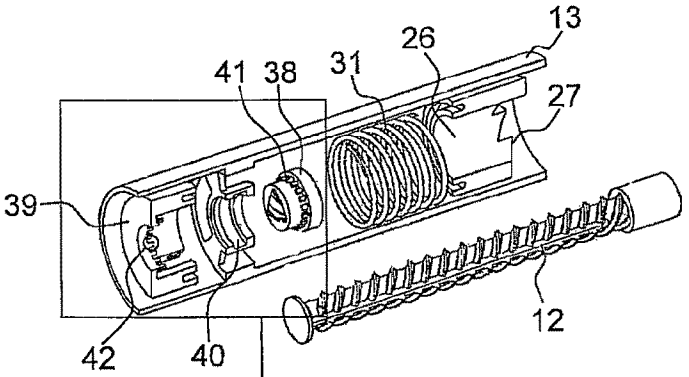
FIG. 4 schematically shows a perspective sectional view of a first embodiment of the reset mechanism in exploded view of the components.

Turning now to FIG. 4, a first embodiment of a resettable drive assembly of the medication delivery device 1 is shown. For setting and dispensing a dose of a medication, the resettable drive assembly comprises the same functional and structural features as described in FIGS. 2 and 3. In FIG. 4, further features of the drive assembly are shown which allow a resetting of the drive assembly. Essential components are depicted in exploded view. FIG. 4 shows a part of the housing 13 with the stop member 26 and its respective toothing 27. As described in FIGS. 2 and 3, the stop member 26 interacts with the drive member 20 for driving the piston rod 12. In FIG. 4 only the stop member 26 is depicted. Furthermore, the resilient member 31 is depicted in FIG. 4, providing a force for engagement and abutment of stop member 26 with the respective drive member 20 and rotation member 21 (see FIGS. 2 and 3).

Besides the function of holding the stop member 26 in engagement with the drive member 20, the resilient member 31 also has the function for providing a force for disengagement of parts of the drive assembly, i.e. a conversion element 38 and coupling means 39, such that a resetting is enabled. The conversion element 38 and coupling means 39 are arranged at a distal end of the housing 13. The resilient member 31 is located such that it may engage with the coupling means 39 on the distal side of resilient member 31 and may engage with the stop member 26 on the proximal side of resilient member 31.

The conversion element 38 can be surrounded and bordered by retaining means 40 which are integrally formed as part of the housing 13 according to the embodiment of FIG. 4. The retaining means 40 prevent the conversion element 38 from axial movement but permit the conversion element 38 to rotate with respect to the housing 13. The conversion element 38 comprises an inner thread for threaded engagement with an outer thread of the piston rod 12. Thus the conversion element 38 acts as "nut means" or "body nut" that guides and holds the piston rod 12. In the operational state of the device 1 when dispensing a dose, rotational movement of the piston rod 12 is thereby converted by the conversion element 38 into helical movement such that the piston rod 12 is axially moved in distal direction through the housing 13.

Preferably, the coupling means 39 is prevented from rotational movement with respect to the housing 13. This can be effected by engagement of the coupling means 39 with at least a part of the housing 13 or a part integrally formed on the inner diameter of the housing 13 or a component fixed to the housing 13, e.g. a spline, protrusion or a connecting element for connecting the retaining means 40 to the housing 13. The coupling means 39 may engage with the at least one connecting element such that rotational movement of the coupling means 39 is inhibited. In the operational state of the device 1 the conversion element 38 interacts with the coupling means 39 such that the conversion element 38 is prevented from rotational movement with respect to the housing via the coupling means 39. For this purpose, the conversion element 38 comprises a first locking means 41 and the coupling means 39 comprises a second locking means 42.

Figure 5:
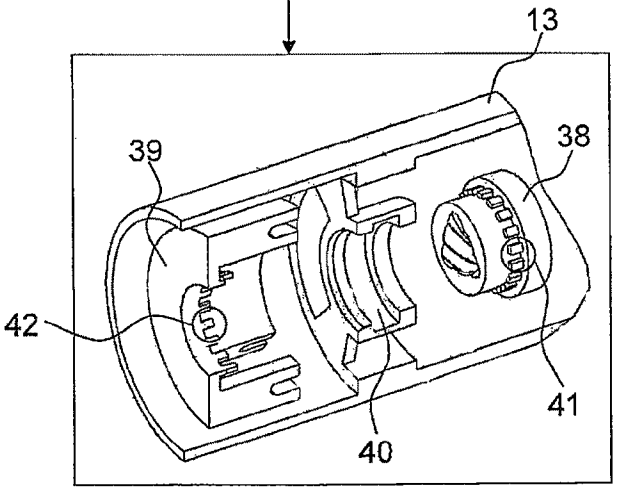
FIG. 5 schematically shows a more detailed perspective sectional view of a part of FIG. 4.

FIG. 5 shows a detailed view of the whole resettable drive assembly comprising the conversion element 38, coupling means 39 and the retaining means 40 arranged within the housing 13. The first and second locking means 41 and 42, according to this embodiment, are designed as teeth. In particular, the teeth of the first locking means 41 are circumferentially arranged at an outer diameter of the conversion element 38. The teeth of the second locking means 42 on the coupling means 39 are arranged at an inner diameter of the coupling means 39 such that they act as a negative form for interlocking with the teeth of the first locking means 41 of the conversion element 38.

According to the embodiment of FIGS. 4 and 5 the conversion element 38 interacts with the retaining means 40 such that the conversion element 38 is permanently secured against axial movement with respect to the housing. The coupling means 39 is designed such that it is axially moveable with respect to the housing and can be brought in a first position according to the operational state, thereby interlocking with the conversion element 38 and can be brought in a second position according to the resetting state thereby being disengaged from the conversion element 38. The resilient member 31 provides a respective force for disengaging the coupling means 39 from the conversion element 38 during switching the device 1 from the operational state into the resetting state.

Figure 6:
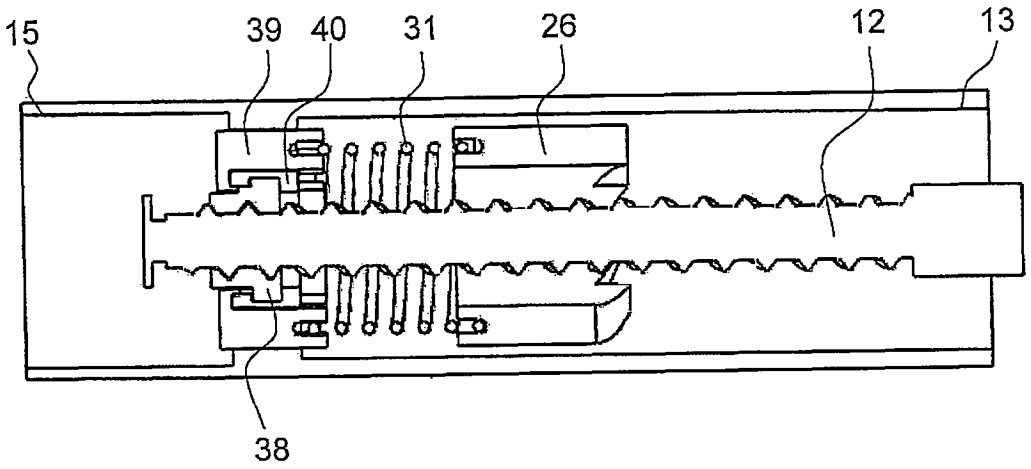
FIG. 6 shows a sectional view of the embodiment according to FIG. 4 in the operational state.

FIG. 6 shows a sectional side view of the components according to FIGS. 4 and 5 which are assembled together. In particular, FIG. 6 shows the operational state of the device 1, wherein the coupling means 39 is located and held in the first position, i.e. in abutment with the conversion element 38, thereby interlocking with the conversion element 38 and preventing it from rotational movement with respect to the housing. The coupling means 39 is preferably held in this position by a proximal end side of a medication receptacle (not shown) which is inserted in and engaged with the distal end side of the housing 13, the proximal end side of the medication receptacle directly or indirectly urging the coupling means 39 to be held in this position against the force of the resilient member 31. Due to the engagement of the coupling means 39 with the conversion element 38, the conversion element 38 is prevented from rotational movement with respect to the housing 13. Furthermore, the piston rod 12 is threadedly engaged with the conversion element 38 such that a rotational movement of the piston rod becomes transmitted into helical and thus axial movement of the piston rod 12. Due to this distal movement a piston or bung or plunger of a cartridge of the medication receptacle (not shown) can be pushed in distal direction for expelling medication out of the cartridge.

FIG. 6 shows the arrangement of the resilient member 31 between the conversion element 38 and the coupling means 39 being engaged to each other on the one side and the stop member 26 on the other side. Due to this arrangement, the resilient member 31 is enabled to fulfil double duties. Firstly, the resilient member 31 provides a force for engagement of the stop member 26 with the drive assembly members as explained above. Secondly, the resilient member 31, as it is strained in the operational state, provides a force on the coupling means that urges the coupling means 39 to be separated and disengaged from the conversion element 38 during switching of the device from the operational state as depicted in FIG. 6 into the resetting state as explained below.

Figure 7:
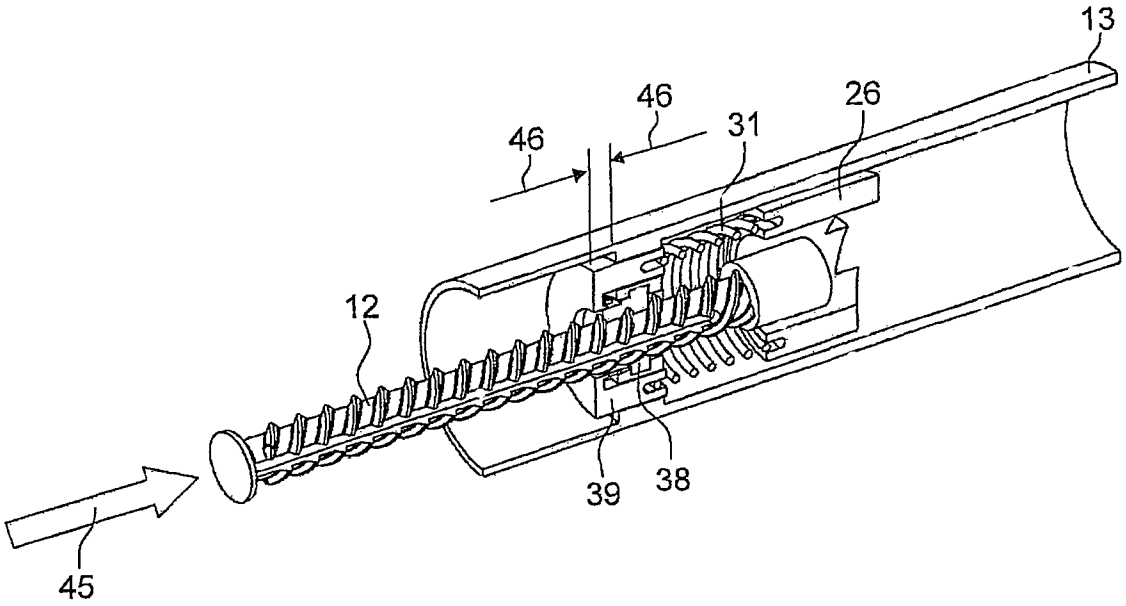
FIG. 7 schematically shows a perspective sectional view of the embodiment according to FIG. 4 in the resetting state.

This resetting state is shown in FIG. 7. A switching from the operational state into the resetting state was initiated by removing the medication receptacle from the housing 13. The resilient member 31 urges the coupling means 39 to move axially away from the conversion element 38, i.e. the coupling means 39 is brought from the first position into a second position. Hence, the device has been switched from the operational state depicted in FIG. 6 into the resetting state depicted in FIG. 7. The traverse path of the coupling means 39 is depicted by respective arrows 46 marking the distance between the first position of the coupling means 39 according to FIG. 6 and the second position of the coupling means 39 according to FIG. 7.

Thus, in the resetting state of FIG. 7, the coupling means 39 is disengaged from the conversion element 38 thereby allowing the conversion element 38 to freely rotate with respect to the housing 13. From this it follows that the piston rod 12 can be moved in proximal direction back into the housing 13. According to FIG. 7, the piston rod is in a position after expelling the last dose of medication and can be moved in proximal direction back into the housing 13. The movement of the piston rod 12 is indicated by the arrow 45 pointing towards the distal end of the piston rod 12. Movement of the piston rod 12 in proximal direction can e.g. be effected by a force which is exerted by a hand of a user or a new cartridge being secured to the housing 13.

The movement of the piston rod 12 results in rotational movement of the conversion element 38 which is free to rotate as described above. Preferably, the thread pitch of the piston rod 12 is to be adapted such that the threaded engagement of the piston rod 12 and the conversion element 38 does not inhibit rotational movement of the conversion element 38 during the resetting of the piston rod 12 back into the housing 13.

Figure 8:
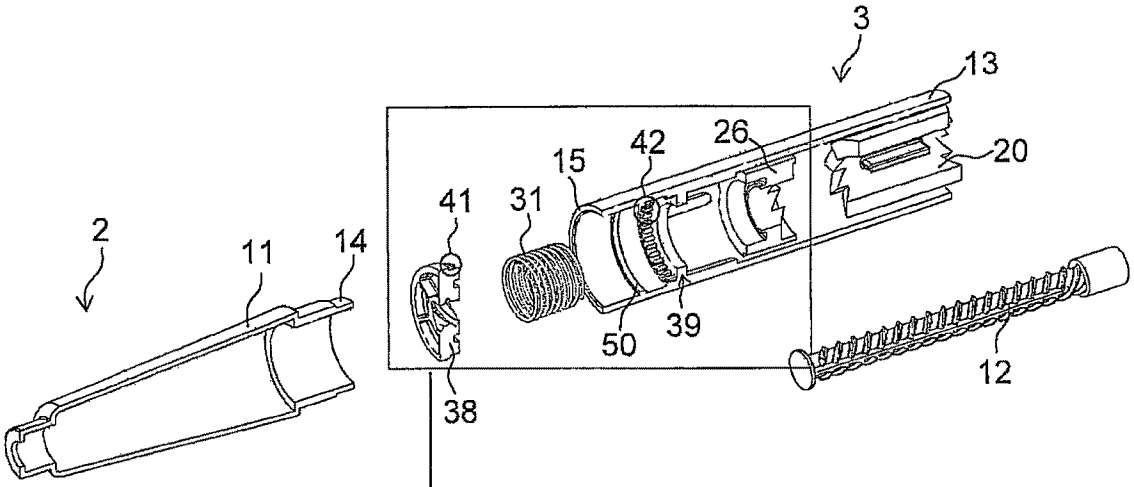
FIG. 8 schematically shows a perspective sectional view of a second embodiment of the reset mechanism in exploded view of the components.

In FIG. 8 another embodiment of a device 1 with a respective resettable drive assembly 3 is depicted in exploded view of the corresponding components. FIG. 8 shows parts of a device 1 according to the description of FIGS. 1 to 3, in particular a medication receptacle 2 with a cartridge retaining member 11 which can be inserted in and engaged at its proximal end side 14 with the distal end side 15 of the housing 13 wherein the drive members are incorporated. In particular, the housing 13 houses a drive member 20 and a stop member 26 which in the operational state are engaged and held in engagement by a force of a resilient member 31. The functionality of the drive member 20 and the stop member 26 has been explained in connection with FIGS. 2 and 3.

Furthermore, the housing 13 houses a conversion element 38 and coupling means 39. According to this embodiment and contrary to the embodiment explained in FIGS. 4 to 7, the conversion element 38 is axially moveable and can be brought and held in a first position according to an operational state of the device and can be brought and held in a second position according to a resetting state of the device due to a force provided by the resilient member 31. The conversion element 38 comprises an inner thread for threaded engagement with an outer thread of the piston rod 12. In the operational state of the device, rotational movement of the piston rod 12 is thereby converted by the conversion element 38 into helical movement such that the piston rod 12 is axially moved in distal direction through the housing 13. The coupling means 39 is integrally formed as part of the housing 13 according to this embodiment.

Figure 9:
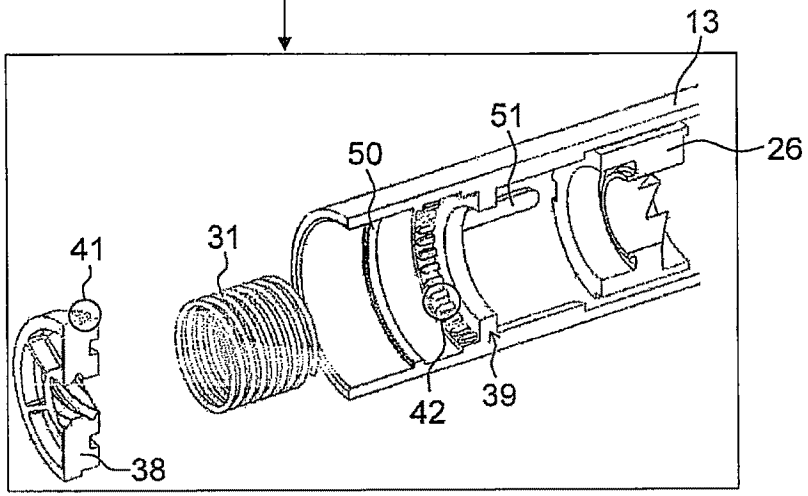
FIG. 9 schematically shows a more detailed perspective sectional view of a part of FIG. 8.

FIG. 9 shows a more detailed view of parts of FIG. 8, especially the conversion element 38 and the coupling means 39 interacting with each other and being separable by the force of the resilient member 31. The conversion element 38 comprises first locking means 41, i.e. teeth, which can be brought into engagement with second locking means 42 of coupling means 39, whereby the second locking means 42 acts as matching teeth for interlocking with the first locking means 41. A circumferential protrusion 50 integrally formed in the inner diameter of the housing 13 is provided for abutment of the conversion element 38 in the second position according to the resetting state of the device after the conversion element 38 has been separated from the coupling means 39 due to the force of the resilient member 31.

The stop member 26 can be secured against rotational movement with respect to the housing by means of at least one protrusion 51 which is integrally formed on the inner diameter of the housing 13 and which interacts with at least one negative form on the outer diameter of the stop member 26.

Figure 10:
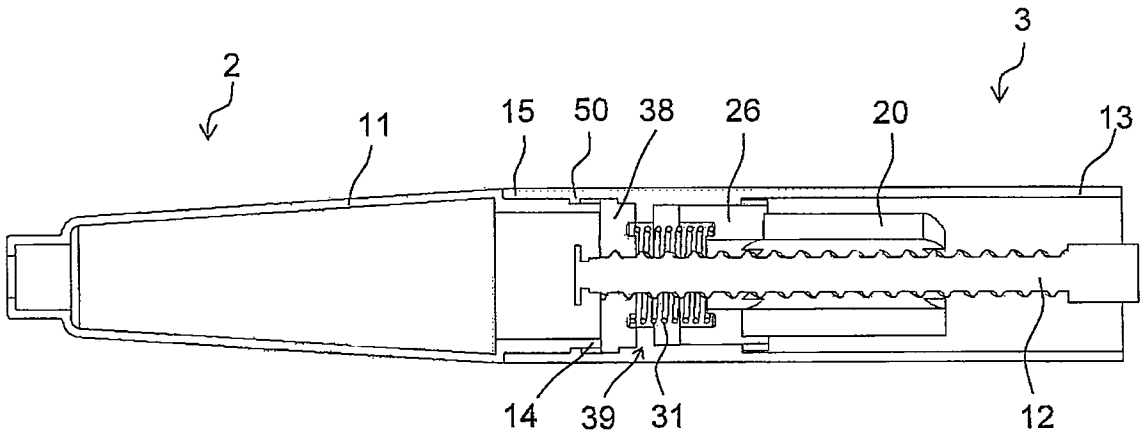
FIG. 10 shows a sectional view of the embodiment according to FIG. 8 in the operational state.

FIG. 10 shows the components of FIGS. 8 and 9 assembled together. In particular, FIG. 10 shows the operational state of the second embodiment according to FIGS. 8 and 9. The medication receptacle 2 with its cartridge retaining member 11 is inserted in and engaged with its proximal end side 14 at the distal end side 15 of the housing 13, thereby pressing the conversion element 38 against the coupling means 39 and holding the conversion element 38 in its position, i.e. in abutment with the coupling means 39. Hence, the conversion element 38 interlocks with the coupling means 39 such that the conversion element 38 is secured against rotational movement with respect to the housing. In this operational state the piston rod 12 which is threadedly engaged with the conversion element 38 can be moved in distal direction pushing a piston or plunger or bung (not shown) of a cartridge within the medication receptacle 2 in distal direction for expelling a medication.

FIG. 10 shows the resilient member 31 being arranged between the conversion element 38 and the coupling means 39 on one side and the drive assembly comprising stop member 26 and drive member 20 on the other side.

Furthermore, the resilient member 31 is strained due to the medication receptacle 2 inserted within the housing 13. In detail, the resilient member 31 pushes the conversion element 38 in proximal direction and thus the conversion element 38 compresses the resilient member 31 which abuts in proximal direction with the stop member 26. Accordingly, the resilient member 31, on the one hand, provides a force for holding the drive member 20 and the stop member 26 in engagement and preferably in abutment with each other and, on the other hand, provides a force for separating the conversion element 38 from the coupling means 39 during the switching of the device from the operational state according to FIG. 10 into the resetting state as explained below.

Figures 11, 12:
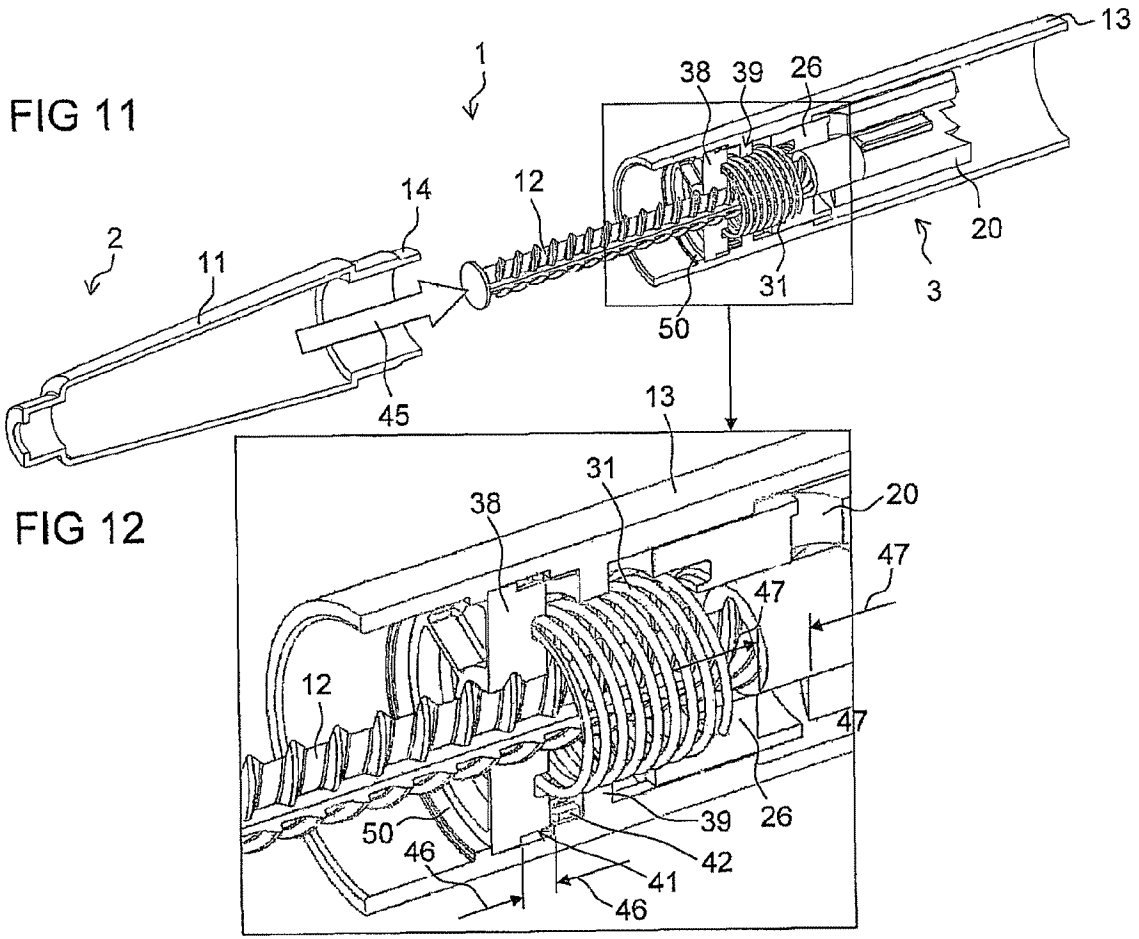
FIG. 11 schematically shows a perspective sectional view of the embodiment according to FIG. 8 in the resetting state.
FIG. 12 schematically shows a more detailed perspective sectional view of a part of FIG. 11.

In FIG. 11 the resetting state of the device is shown. Switching of the device 1 from the operational state according to FIG. 10 and the resetting state according to FIG. 11 was initiated with the medication receptacle 2 being removed from the housing 13. The resilient member 31 becomes unstrained urging the conversion element 38 to be separated and disengaged from the coupling means 39 in distal direction. The conversion element 38 is free to rotate. Hence, the piston rod 12 can be moved in proximal direction back into the housing 13 as indicated by the arrow 45 pointing towards the distal end of the piston rod 12. According to FIG. 11 the piston rod is in a position after expelling the last dose of medication.

FIG. 12 shows a detailed view of parts of FIG. 11. Due to the force of the resilient member 31, on the one hand, the conversion element 38 has become separated from the coupling means 39, the first locking means 41 being disengaged from the second locking means 42, i.e. the respective circumferential teeth being separated from each other. The conversion element 38 is brought and held in the second position according to the resetting state whereby the traverse path of the conversion element between the first position and the second position is depicted by two arrows 46 marking the distance between the first and second position. Preferably, in this resetting state the resilient member 31 provides no more force for holding the stop member 26 and drive member 20 in engagement such that drive member 20 and stop member 26 can be separated from each other, thereby bringing the drive member 20 in a position away from the stop member 26. This traverse path is also depicted by second arrows 47 marking the distance between the drive member 20 and the stop member 26. But it is also conceivable that stop member 26 and drive member 20 remain in engagement with each other.

In this resetting state of FIG. 12 the piston rod 12 can be moved in proximal direction back into the housing, whereby the conversion element 38 is free to rotate with respect to the housing such that a resetting of the piston rod 12 is possible. Preferably, the thread pitch of the piston rod 12 is adapted such that rotational movement of the conversion element 38 is not inhibited. The piston rod 12 either can be exclusively axially moved in proximal direction without rotation of the piston rod, the drive member 20 thereby not rotating. But it is also conceivable that the piston rod 12 can be helically moved back into the housing 13 due to the separation of the drive member 20 from the stop member 26, the drive member 20 thereby freely rotating with respect to the housing 13 due to disengagement from the stop member 26.

In general, the medication delivery device with its reset mechanism as described and explained above provides for a smooth and easy reset action and aids all users, but particularly those with impaired dexterity. Furthermore, the device is cost-effective with its sole resilient member fulfilling double duties. The embodiments described above are exemplary and do not restrict the invention.

We claim:

1. A medication delivery device being switchable between an operational state and a resetting state, comprising:

a housing having a proximal end and a distal end, a piston rod being moveable in a distal direction with respect to the housing for medication delivery, a conversion element adapted to at least partially convert a rotational movement of the piston rod into an axial movement of the piston rod, coupling means prevented from rotational movement with respect to the housing and adapted to engage with the conversion element in the operational state, a drive assembly comprising at least two drive assembly members and adapted for moving the piston rod in the distal direction, a resilient member adapted to provide a force on the drive assembly for engagement of the drive assembly members, wherein in the operational state of the device the coupling means is engaged with the conversion element, the conversion element thereby being prevented from rotation with respect to the housing, and in the resetting state of the device the coupling means is disengaged from the conversion element under force of the resilient member, the conversion element thereby being allowed to rotate with respect to the housing and thereby allowing a resetting of the device.

2. The medication delivery device according to claim 1, wherein the conversion element is permanently prevented from axial movement with respect to the housing, and during switching of the device between the operational state and the resetting state the coupling means is axially moved with respect to the housing between a first axial position according to the operational state of the device and a second axial position according to the resetting state of the device.

3. The medication delivery device according to claim 2, comprising retaining means prevented from axial movement relative to the housing, the conversion element being restrained by the retaining means from moving axially and being allowed to revolve with respect to the housing.

4. The medication delivery device according to claim 2, wherein in the operational state of the device the coupling means is held in the first axial position, and during switching of the device between the operational state and the resetting state the coupling means is axially moved and brought into the second axial position under force of the resilient member.

5. The medication delivery device according to claim 1, wherein the coupling means is permanently prevented from axial movement with respect to the housing, and during switching of the device between the operational state and the resetting state the conversion element is axially moved with respect to the housing between a first axial position according to the operational state of the device and a second axial position according to the resetting state of the device.

6. The medication delivery device according to claim 5, wherein in the operational state of the device the conversion element is held in the first axial position, and during switching of the device between the operational state and the resetting state the conversion element is moved in distal direction and brought into the second axial position under force of the resilient member.

7. The medication delivery device according to claim 1, comprising a medication receptacle adapted to be secured to the housing wherein in the operational state of the device the medication receptacle is secured to the housing thereby holding the coupling means in engagement with the conversion element, and in the resetting state of the device the medication receptacle is removed from the housing thereby allowing disengagement of the coupling means from the conversion element.

8. The medication delivery device according to claim 1, wherein the conversion element comprises first locking means and the coupling means comprises second locking means, the first and second locking means being adapted to interlock with each other.

9. The medication delivery device according to claim 8, wherein the first and second locking means are formed by at least one of teeth, splines, protrusions, and castellations.

10. The medication delivery device according to claim 1, wherein the piston rod is threadedly engaged with the conversion element.

11. The medication delivery device according to claim 1, [comprising] *where one of the two drive assembly members comprises* a rotation member which is adapted to be rotated in a first direction with respect to the housing during setting of a dose of a medication and to be rotated in a second direction with respect to the housing during delivery of the dose, the second direction being opposite to the first direction.

12. The medication delivery device according to claim [1] *11*, [comprising] *where one of the two drive assembly members comprises* a drive member which is adapted to be rotated with respect to the housing, wherein rotational movement of the drive member with respect to the housing is converted into movement of the piston rod in the distal direction with respect to the housing.

13. The medication delivery device according to claim [11] *12*, wherein in the operational state the drive member is adapted to follow rotational movement of the rotation member in the second direction with respect to the housing during delivery of the dose.

14. The medication delivery device according to claim 13, wherein the drive member and the rotation member are coupled to one another by a first uni-directional friction clutch mechanism which is configured to permit relative rotational movement between the drive member and the rotation member during rotation of the rotation member in the first direction for setting of the dose and to prevent relative rotational movement of drive member and rotation member during rotation of the rotation member in the second direction for delivery of the dose.

15. The medication delivery device according to claim 12, wherein the drive member is engaged with a stop member which is adapted to prevent rotational movement of the drive member in the first direction with respect to the housing and to permit rotational movement of the drive member in the second direction with respect to the housing.

16. The medication delivery device according to claim 15, wherein the drive member and the stop member are coupled to one another by a second uni-directional friction clutch mechanism, which is configured to prevent relative rotational movement between the drive member and the stop member in the first direction with respect to the housing and to permit relative rotational movement between the drive member and the stop member in the second direction with respect to the housing.

*17. A medication delivery device being switchable between an operational state and a resetting state, comprising:*

*a housing having a proximal end and a distal end,*

*a piston rod being moveable in a distal direction with respect to the housing for medication delivery,*

*a nut configured to cause an axial movement of the piston rod when the device is in the operational state,*

*a coupling prevented from rotational movement with respect to the housing and configured to engage with the nut in the operational state,*

*a drive assembly comprising at least two drive assembly members and adapted for moving the piston rod in the distal direction,*

*a resilient member configured to provide an axial biasing force on the coupling in the operational state,*

*wherein in the operational state the coupling is engaged with the nut, the nut thereby being prevented from rotation with respect to the housing, and*

*in the resetting state the coupling is disengaged from the nut under the biasing force of the resilient member, the nut thereby being allowed to rotate with respect to the housing and thereby allowing a resetting of the device.*

*18. A medication delivery device being switchable between an operational state and a resetting state, comprising:*

*a housing having a proximal end and a distal end,*

*a piston rod being moveable in a distal direction with respect to the housing for medication delivery,*

*a guide component configured to cause an axial movement of the piston rod when the device is in the operational state,*

*a coupling prevented from rotational movement with respect to the housing and configured to engage with the guide component in the operational state,*

*a drive assembly comprising at least two drive assembly members and adapted for moving the piston rod in the distal direction,*

*a resilient member configured to provide an axial biasing force on the coupling in the operational state,*

*wherein in the operational state the coupling is engaged with the guide component, the guide component thereby being prevented from rotation with respect to the housing, and*

*in the resetting state the coupling is disengaged from the guide component under the biasing force of the resilient member, the guide component thereby being allowed to rotate with respect to the housing and thereby allowing a resetting of the device.*

* * * * *